United States Patent
Namkoong et al.

(10) Patent No.: US 12,390,405 B2
(45) Date of Patent: Aug. 19, 2025

(54) PERSONAL CARE COMPOSITIONS

(71) Applicant: Colgate-Palmolive Company, New York, NY (US)

(72) Inventors: Jin Namkoong, High Bridge, NJ (US); Qiang Wu, Hillsborough, NJ (US); Thomas Boyd, Metuchen, NJ (US); Ewelina Lesniak, Linden, NJ (US); Melissa Moy, Staten Island, NY (US); Vinay Bhardwaj, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 226 days.

(21) Appl. No.: 18/083,840

(22) Filed: Dec. 19, 2022

(65) Prior Publication Data
US 2023/0201094 A1 Jun. 29, 2023

Related U.S. Application Data

(60) Provisional application No. 63/340,382, filed on May 10, 2022, provisional application No. 63/293,258, filed on Dec. 23, 2021.

(51) Int. Cl.
| | |
|---|---|
| *A61K 8/34* | (2006.01) |
| *A61K 8/02* | (2006.01) |
| *A61K 8/44* | (2006.01) |
| *A61K 8/67* | (2006.01) |
| *A61K 8/73* | (2006.01) |
| *A61K 8/9789* | (2017.01) |
| *A61K 31/728* | (2006.01) |
| *A61M 37/00* | (2006.01) |
| *A61P 17/02* | (2006.01) |
| *A61Q 19/02* | (2006.01) |

(52) U.S. Cl.
CPC ............ *A61K 8/347* (2013.01); *A61K 8/0208* (2013.01); *A61K 8/34* (2013.01); *A61K 8/44* (2013.01); *A61K 8/675* (2013.01); *A61K 8/735* (2013.01); *A61K 8/9789* (2017.08); *A61K 31/728* (2013.01); *A61M 37/0015* (2013.01); *A61P 17/02* (2018.01); *A61Q 19/02* (2013.01); *A61K 2800/30* (2013.01); *A61K 2800/48* (2013.01); *A61K 2800/87* (2013.01); *A61K 2800/88* (2013.01); *A61K 2800/91* (2013.01); *A61M 2037/0023* (2013.01); *A61M 2037/0046* (2013.01)

(58) Field of Classification Search
None
See application file for complete search history.

(56) References Cited

U.S. PATENT DOCUMENTS

| | | |
|---|---|---|
| 8,236,288 B2 | 8/2012 | Mehta et al. |
| 2012/0177586 A1* | 7/2012 | Mehta .................. A61K 8/4926 424/59 |

FOREIGN PATENT DOCUMENTS

| | | | |
|---|---|---|---|
| CN | 113893197 A * | 1/2022 | ........... A61K 8/0208 |
| WO | 2012/094638 | 7/2012 | |

OTHER PUBLICATIONS

Chaudhuri, "Hexylresorcinol: Providing Skin Benefits by Modulating Multiple Molecular Targets" In: "Cosmeceuticals and Active Cosmetics", CRC Press: 70-75, 2015.

International Search Report and the Written Opinion of the International Searching Authority issued in International Application PCT/US2022/053330 mailed May 10, 2023.

Xing et al., "Novel dissolving microneedles preparation for synergistic melasma therapy: Combined effects of tranexamic acid and licorice extract", International Journal of Pharmaceutics, Elsevier, vol. 600, 2021.

Zaid et al., "Depigmentation and anti-aging treatment by natural molecules", Current Pharmaceutical Design, Bentham Science Publishers Ltd., 25(20):2292-2312, 2019.

* cited by examiner

*Primary Examiner* — Nannette Holloman

(57) ABSTRACT

Disclosed are skin lightening personal care compositions comprising hexylresorcinol and licorice extract, wherein hexylresorcinol is present in an amount of from 0.00001% to 1% by weight of the composition and licorice extract is present in an amount of from 0.00001% to 0.1% by weight of the composition, as well as methods of using these compositions.

19 Claims, 1 Drawing Sheet

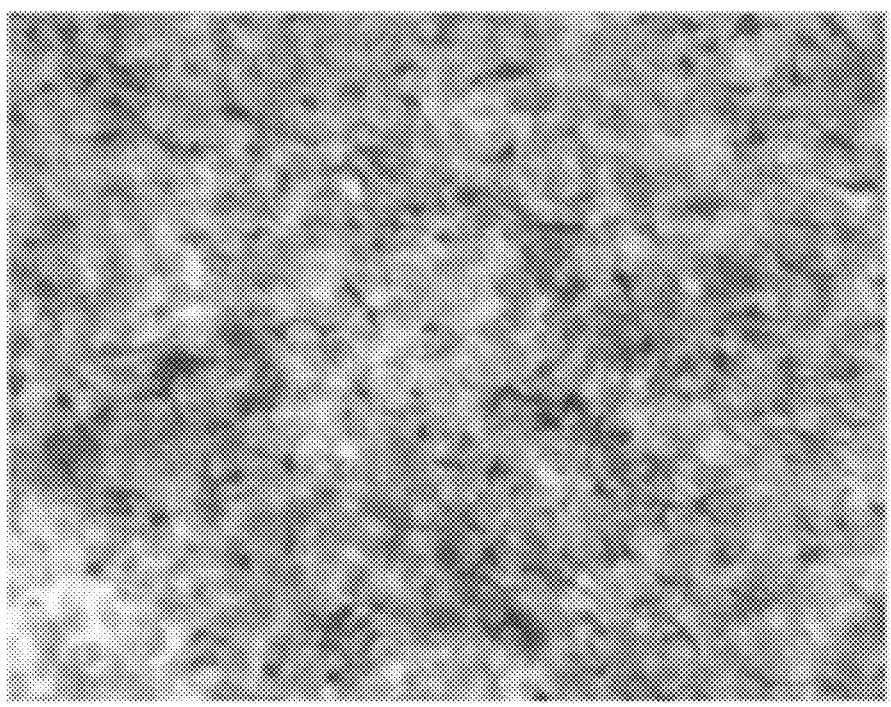

PERSONAL CARE COMPOSITIONS

CROSS-REFERENCE TO RELATED APPLICATIONS

This application is a U.S. Non-Provisional Application under 35 U.S.C. § 111 (a), which claims priority to and the benefit of U.S. Provisional Application Ser. No. 63/293,258, filed on Dec. 23, 2021, and U.S. Provisional Application Ser. No. 63/340,382, filed on May 10, 2022, the contents of which are hereby incorporated by reference in their entireties.

BACKGROUND

Skin coloration arises from a complex series of cellular processes in the population of cells known as melanocytes, located in the lower part of the epidermis. These processes result in the synthesis of a pigment, melanin, which besides being responsible for skin color and tone, is the key physiological defense against sun-induced damage, photoaging and photocarcinogenesis. As a result of the aging process, sun damage or exposure to environmental pollutants, skin may become hyperpigmented, have dark spots and/or become wrinkled. Consumers are concerned about their appearance and look for skin products to treat discoloration, hyperpigmentation and dark spots. Skin lightening products are in big demand across the globe.

Skin lightening products work by reducing the amount of melanin in the skin. Many common skin lightening ingredients in the cosmetic market are reported to be unsafe, cytotoxic, unstable or ineffective at low concentrations. The most common lightening ingredients used today are kojic acid and hydroquinone. However, kojic acid and hydroquinone are known for their toxic action on skin cells and therefore their cosmetic use has been restricted or banned in many countries. When an ingredient(s) in skin lightening products impacts the viability of melanocytes, it results in skin hypopigmentation or a white spot on the skin. Reducing melanin produced by melanocytes without impacting the viability of melanocytes will result in skin lightening without unwanted skin hypopigmentation or a white spot on the skin. There is a need for skin lightening products which suppress melanin synthesis but do not impact the viability of melanocytes.

SUMMARY OF THE INVENTION

In one aspect, the invention provides a personal care composition, e.g., skin lightening composition, comprising hexylresorcinol and licorice extract, wherein hexylresorcinol is present in an amount of from 0.00001% to 1% by weight of the composition and licorice extract is present in an amount of from 0.00001% to 0.1% by weight of the composition. In some embodiments, the licorice extract is licorice root extract. In some embodiments, the licorice extract is *Glycyrrhiza Glabra* root extract.

In some embodiments, the personal care composition may comprise additional skin lightening agents other than the hexylresorcinol and the licorice extract, e.g., selected from 4-butyl resorcinol, niacinamide, tranexamic acid and bisabolol, and a combination thereof. In certain embodiments, the personal care composition comprises 4-butyl resorcinol, niacinamide, tranexamic acid and bisabolol. In certain embodiments, the personal care composition comprises 0.4-0.6% hexylresorcinol, 0.02-0.04% licorice extract, 0.04-0.2% 4-butyl resorcinol, 3-6% niacinamide, 1-5% tranexamic acid and 0.4-0.6% bisabolol.

In some embodiments, the personal care composition is free of kojic and hydroquinone free. In some embodiments, the personal care composition is free of substituted benzaldehydes. In some embodiments, the personal care composition is free of kojic acid, hydroquinone, and substituted benzaldehydes.

In some embodiments, the personal care composition is a leave-on composition. In some embodiments, the leave-on composition is a cream, lotion, or serum. In other embodiments, the composition is a rinse-off composition. In some embodiments, the rinse-off composition is a liquid soap, hand soap, face soap, shower gel, body wash, shampoo, or hair conditioner.

In some embodiments, the hexylresorcinol is present in an amount of from 0.01% to 1%, from 0.05% to 1%, from 0.2% to 1%, from 0.4% to 1%, from 0.4% to 0.8%, from 0.4% to 0.6%, or about 0.5%, by weight of the composition.

In some embodiments, the licorice extract is present in an amount of from 0.001% to 0.05%, from 0.003% to 0.05%, from 0.01% to 0.05%, from 0.02% to 0.04%, about 0.03%, or 0.03125%, by weight of the composition.

In some embodiments, the weight ratio of the hexylresorcinol to the licorice extract present in the personal care composition is in the range of from 10:1 to 25:1, from 10:1 to 20:1, from 14:1 to 18:1 or about 16:1.

In some embodiments, the personal care compositions of the disclosure can be delivered to the skin using a microneedle patch. For example, the microneedle patch can comprise dissolvable microneedles. In certain embodiments the personal care composition delivered via the microneedle patch (e.g., the dissolvable microneedle patch) comprises hexylresorcinol and licorice extract, wherein hexylresorcinol is present in an amount of from 0.00001% to 1% by weight of the composition and licorice extract is present in an amount of from 0.00001% to 0.1% by weight of the composition. In a further aspect, in addition to hexylresorcinol and licorice extract, the personal care composition further comprises hyaluronic acid ("HA"). In certain aspects the HA is acetylated HA. In some aspects the "HA" has a low average molecular weight, e.g., less than or equal to 50 kDa (e.g., from 10 kDa-40 kDa) (e.g., avg 20 kDa) (e.g., avg 30 kDa), and can be optionally acetylated. In certain aspects both the microneedle patch, and the personal care composition delivered via the microneedle patch, each comprise hyaluronic acid ("HA").

In another aspect, the invention provides a method of suppressing melanin synthesis in melanocytes in the skin, comprising applying an effective amount of any of personal care compositions as disclosed herein to the skin, e.g., any of Composition 1.0 et seq.

In another aspect, the invention provides a method of post-inflammatory hyperpigmentation in the skin, comprising applying an effective amount of any of personal care compositions as disclosed herein to the skin, e.g., any of Composition 1.0 et seq.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

BRIEF DESCRIPTION OF THE DRAWINGS

FIG. 1 shows a microscopic image of MelanoDerm tissue treated with a cleanser (Composition 1) at day 15.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight. The amounts given are based on the active weight of the material.

Hexylresorcinol is an organic compound with antiseptic, local anesthetic, and anthelmintic properties. It is currently being used as an antiseptic in many cosmetic products. It is also used topically on small skin infections, or as an ingredient in throat lozenges. The structure of hexylresorcinol is shown below:

hexylresorcinol

Licorice is the common name of *Glycyrrhiza glabra*, a flowering plant of the bean family Fabaceae. It has been reported that licorice extract, e.g., licorice root extract, lightens the skin color. Licorice extract contains liquiritin and licochalcone. These compounds are known to inhibit melanocytes from making tyrosinase. This slows down the production of melanin in the skin, thus lightening skin color.

The present invention relates to the use of hexylresorcinol and licorice extract at certain concentrations in skin lightening compositions. In the present invention, it has been found that hexylresorcinol and licorice extract have activity to inhibit melanin synthesis in human melanocytes. Furthermore, it has been surprisingly found that the combination of hexylresorcinol and licorice extract at certain concentrations delivers synergistic benefits to inhibit melanin synthesis in human melanocytes. This is important, because the synergy allows hexylresorcinol and licorice extract to be used at low concentrations in skin lightening products. Active ingredients in skin lightening products may impact the viability of melanocytes, resulting in skin hypopigmentation or a white spot on the skin and/or may also cause other side effects such as allergy and skin irritation. Thus, the use of active ingredients at low concentrations in skin lightening products would be beneficial, because it may decrease the cytotoxicity of the ingredients and/or prevent or reduce any other side effects such as allergy and skin irritation. The synergy between hexylresorcinol and licorice extract allows for the use of the compounds at low concentrations to formulate skin lightening products which do not affect the viability of melanocytes significantly but still suppress melanin synthesis in melanocytes.

The present invention provides, in an aspect, a personal care composition (Composition 1.0), e.g., skin lightening composition, comprising hexylresorcinol and licorice extract, wherein hexylresorcinol is present in an amount of from 0.00001% to 1% by weight of the composition and licorice extract is present in an amount of from 0.00001% to 0.1% by weight of the composition.

For example, the invention includes:
1.1. Composition 1.0, wherein the licorice extract is licorice root extract, optionally wherein the licorice extract is *Glycyrrhiza Glabra* root extract.
1.2. Composition 1.0 or 1.1, wherein the personal care composition is a skin lightening composition.
1.3. Any of preceding compositions, wherein the personal care composition is selected from the group consisting of creams, lotions, serums, antiperspirants, deodorants, body washes, liquid soaps, hand soaps, face soap, shower gels, bar soaps, shampoos, hair conditioners, and cosmetics.
1.4. Any of preceding compositions, wherein the personal care composition comprises additional skin lightening agents other than the hexylresorcinol and the licorice extract, optionally wherein the addition skin lightening agents is selected from 4-butyl resorcinol, niacinamide, tranexamic acid and bisabolol, and a combination thereof.
1.5. Any of preceding compositions, wherein the personal care composition comprises 4-butyl resorcinol, niacinamide, tranexamic acid and bisabolol, optionally wherein the personal care composition comprises 0.4-0.6% hexylresorcinol, 0.02-0.04% licorice extract, 0.04-0.2% 4-butyl resorcinol, 3-6% niacinamide, 1-5% tranexamic acid and 0.4-0.6% bisabolol.
1.6. Any of preceding compositions, wherein the personal care composition is free of kojic acid and/or hydroquinone.
1.7. Any of preceding compositions, wherein the personal care composition is free of substituted benzaldehydes.
1.8. Any of preceding compositions, wherein the personal are composition is free of 2-ethoxybenzaldehyde, 4-ethoxybenzaldehyde, 4-allyloxybenzaldehyde, and 4-propoxybenzaldehyde.
1.9. Any of preceding compositions, wherein the personal care composition is free of kojic acid, hydroquinone, and substituted benzaldehydes.
1.10. Any of preceding compositions, wherein the personal care composition is a leave-on composition, optionally wherein the personal care composition is a cream, lotion, or serum.
1.11. Any of preceding compositions, wherein the composition is a rinse-off composition, optionally wherein the rinse-off composition is a liquid soap, hand soap, face soap, shower gel, body wash, shampoo, or hair conditioner.
1.12. Any of preceding compositions, wherein the hexylresorcinol is present in an amount of from 0.01% to 1%, from 0.05% to 1%, from 0.2% to 1%, from 0.4% to 1%, from 0.4% to 0.8%, from 0.4% to 0.6%, or about 0.5%, by weight of the composition.
1.13. Any of preceding compositions, wherein the licorice extract is present the licorice extract is present in an amount of from 0.001% to 0.05%, from 0.003% to 0.05%, from 0.01% to 0.05%, from 0.02% to 0.04%, about 0.03%, or 0.03125%, by weight of the composition.
1.14. Any of preceding compositions, wherein the weight ratio of the hexylresorcinol to the licorice extract present in the personal care composition is in the range of from 10:1 to 25:1, from 10:1 to 20:1, from 14:1 to 18:1 or about 16:1.

1.15. Any of preceding compositions, wherein the personal care composition is a leave-on composition, e.g., cream, lotion, or serum, and the hexylresorcinol is present in an amount of from 0.4% to from 1%, and the licorice extract is present in an amount of from 0.01% to 0.05%, by weight of the composition, optionally wherein the hexylresorcinol is present in an amount of from 0.4% to from 0.6%, and the licorice extract is present in an amount of from 0.02% to 0.04%, by weight of the composition, further optionally wherein the hexylresorcinol is present in an amount of about 0.5% and the licorice extract is present in an amount of about 0.3% or 0.3125%, by weight of the composition.

1.16. Any of preceding compositions, wherein the personal care composition is a rinse-off composition, e.g., a liquid soap, hand soap, face soap, shower gel, body wash, shampoo, or hair conditioner, and the hexylresorcinol is present in an amount of from 0.05% to from 1%, and the licorice extract is present in an amount of from 0.003% to 0.05%, by weight of the composition, optionally wherein the hexylresorcinol is present in an amount of from 0.4% to from 0.6%, and the licorice extract is present in an amount of from 0.02% to 0.04%, by weight of the composition, further optionally wherein the hexylresorcinol is present in an amount of about 0.5% and the licorice extract is present in an amount of about 0.3% or 0.3125%, by weight of the composition.

1.17. Any of the preceding compositions, wherein the composition comprises a thickener.

1.18. Any of the preceding compositions, wherein the thickener comprises sodium polyacryloyldimethyl taurate, optionally wherein sodium polyacryloyldimethyl taurate is present in an amount of 1-3%, e.g., about 2%, by weight of the composition.

1.19. Any of the preceding compositions, wherein the composition comprises a humectant.

1.20. Any of the preceding compositions, wherein the humectant comprises 1,3-butylene glycol, optionally wherein 1,3-butylene glycol in present in an amount of 4-6%, e.g., about 5%, by weight of the composition.

1.21. Any of the preceding compositions, wherein the humectant comprises hyaluronic acid, optionally wherein hyaluronic acid is present in an amount of 0.1-0.3%, e.g., about 0.2%, by weight of the composition.

1.22. Any of the preceding compositions, wherein the composition comprises hyaluronic acid and 1,3-butylene glycol, optionally wherein 1,3-butylene glycol in present in an amount of 4-6%, e.g., about 5%, by weight of the composition and hyaluronic acid is present in an amount of 0.1-0.3%, e.g., about 0.2%, by weight of the composition.

1.23. Any of the preceding compositions, wherein the composition comprises penetration agents.

1.24. Any of the preceding compositions, wherein the penetration agent is selected from ethyl alcohol, witch hazel, urea, fatty acids, glycols, hyaluronic acid and a combination thereof.

1.25. Any of the preceding compositions, wherein the penetration agent comprises hazel and ethanol, optionally wherein witch hazel is present in an amount of 5-15% and ethanol is present 10-20%, by weight of the composition, further optionally wherein witch hazel is present in an amount of 8-12%, e.g., about 10% and ethanol is present 13-17%, about 15%, by weight of the composition.

1.26. Any of the preceding compositions, wherein the composition comprises a polyhydroxy acid, optionally wherein the polyhydroxy acid is selected from gluconolactone, gluconic acid, galactose, lactobionic acid, and a combination thereof, further optionally wherein the composition comprises gluconolactone, e.g., in an amount of 1-3%, e.g., about 2%, by weight of the composition.

1.27. Any of the preceding compositions, wherein the composition comprises an alpha hydroxy acid, optionally wherein the alpha hydroxy acid is selected from mandelic acid, glycolic acid, citric acid, lactic acid, malic acid, tartaric acid, phytic acid, hydroxycaprylic acid, hydroxycapric acid, and a combination thereof, further optionally wherein the composition comprises lactic acid, e.g., in an amount of 4-5%, e.g., about 4%, by weight of the composition.

1.28. Any of the preceding compositions, wherein the composition comprises a combination of pentane-1,2-diol, *Rosa Damascena* Flower extract and rose oils.

1.29. Any of the preceding compositions, wherein the composition an antioxidant, optionally wherein the antioxidant is selected from citric acid, butylated hydroxytoluene, pentaerythrityl tetra-di-t-butyl hydroxyhydrocinnamate and propyl gallate, further optionally wherein the composition comprises propyl gallate, e.g., in an amount of 0.1-0.3%, e.g., about 0.2%, by weigh of the composition.

1.30. Any of the preceding compositions, wherein the composition comprises water.

1.31. Any of the preceding compositions, wherein the composition further comprises a surfactant, an antiperspirant active, a deodorant active, a gelling agent, an antioxidant, a fragrance, or a combination thereof.

1.32. Any of the preceding compositions, wherein the composition comprises 0.4-0.6% hexylresorcinol, 0.02-0.04% licorice extract, 0.04-0.2% 4-butyl resorcinol, 3-6% niacinamide, 1-5% tranexamic acid and 0.4-0.6% bisabolol, 4-6% 3-butylene glycol, 0.1-0.3% hyaluronic acid, 1-3% sodium polyacryloyldimethyl taurate, 8-12% witch hazel, 13-17% ethanol, by weight of the composition, optionally wherein the composition further comprises 0.1-0.3% hyaluronic acid by weight of the composition.

1.33. Any of the preceding personal care compositions, wherein the personal care composition is delivered within a patch (e.g., a transdermal patch) (e.g., a microneedle patch).

1.34. The personal care composition of 1.33, wherein personal care composition is delivered within a microneedle patch.

1.35. The personal care composition of 1.34, wherein the microneedle is selected from the group consisting of: a solid microneedle, a coated microneedle, a dissolvable microneedle, a hollow microneedle, a hydrogel-forming microneedle, and combinations thereof.

1.36. The personal care composition of any of 1.34-1.35, wherein the microneedle is a dissolvable microneedle.

1.37. The personal care composition of 1.36, wherein the dissolvable microneedle comprises one or more biodegradable polymer(s).

1.38. The personal care composition of 1.37, wherein the one or more biodegradable polymer(s) is water-soluble.

1.39. The personal care composition of 1.37 or 1.38, wherein the one or more biodegradable polymer comprises a biodegradable polymer selected from the group consisting of: cross-linked or non-cross-linked bio-absorbable and bio-compatible polymer, (e.g., hyaluronic acid), polyvinylpyrrolidone, polyvinyl alcohol, silkworm sericin, collagen, bio-absorbable sugar, collagen, maltose, galactose, glucose, sucrose, fructose, xylose, xylitol, sorbitol and combinations thereof.

1.40. The personal care composition of 1.39, wherein the biodegradable polymer comprises hyaluronic acid (e.g., from 10%-75% by wt.) or orally acceptable salts and derivatives thereof (e.g., sodium hyaluronate).

1.41. The personal care composition of 1.40, wherein the hyaluronic acid has an average molecular weight of ≤100 kDa (e.g., ≤50 kDa) (e.g., from 10-40 kDa) (e.g., from 20-30 kDa).

1.42. The personal care composition of 1.40 or 1.41, wherein the hyaluronic acid is acetylated (e.g., 30 KDa acetylated HA).

1.43. The personal care composition of 1.40, 1.41 or 1.42, wherein the biodegradable polymer comprises hyaluronic acid and sucrose (e.g., in a weight ratio of 1:1) in a weight ratio of 1.5:1).

1.44. The personal care composition of 1.40, 1.41 or 1.42, wherein the biodegradable polymer comprises hyaluronic acid and silkworm sericin (e.g., in a weight ratio of 1:1) in a weight ratio of 1.5:1).

1.45. The personal care composition of 1.40, 1.41 or 1.42, wherein the biodegradable polymer comprises hyaluronic acid, polyvinylpyrollidone and sucrose (e.g., in a weight ratio of 50:30:20, respectively).

1.46. The personal care composition of any of 1.33 to 1.45, wherein the patch is a microneedle patch, and wherein the average distance between each microneedle is in a range from 20 to 10,000 microns (e.g., a range from 100 to 500 microns).

1.47. The personal care composition of any of 1.33 to 1.46, wherein the patch is a microneedle patch, and wherein the average length of each microneedle is in a range from 50 to 3,000 microns (e.g., a range from 50 to 1,500 microns).

1.48. The personal care composition of any of 1.34-1.47, wherein in the microneedle patch comprises hexylresorcinol and licorice extract.

1.49. The personal care composition of 1.48, wherein the hexylresorcinol is present from 0.01% to 1% by wt. of the composition (e.g., about 0.5% by wt.) and the licorice extract is present from 0.01% to 0.05% by wt. of the composition (e.g., about 0.03125% by wt.).

1.50. The personal care composition of 1.49, wherein the personal care composition is delivered within a microneedle patch, wherein the microneedle patch comprises:
a dissolvable microneedle, wherein the dissolvable microneedle comprises a water-soluble biodegradable polymer (e.g., hyaluronic acid), and wherein the dissolvable microneedle further comprises hexylresorcinol present from 0.01% to 1% by wt. of the composition (e.g., about 0.5% by wt.) and licorice extract present from 0.01% to 0.05% by wt. of the composition (e.g., about 0.03125% by wt.).

1.51. The personal care composition of 1.49 or 1.50, wherein the personal care composition is delivered from within a microneedle patch, wherein the microneedle patch comprises:
a dissolvable microneedle, wherein the dissolvable microneedle comprises hyaluronic acid ("HA") (e.g., HA having a molecular weight of ≤50 kDa) (e.g., from 10-40 kDa) (e.g., from 20-30 kDa) (e.g., wherein the HA is acetylated); and wherein the dissolvable microneedle further comprises hexylresorcinol present from 0.01% to 1% by wt. of the composition (e.g., about 0.5% by wt.) and licorice extract present from 0.01% to 0.05% by wt. of the composition (e.g., about 0.03125% by wt.).

1.52. The personal care composition of any of 1.34-1.51, wherein the microneedle patch optionally comprises a moisture pad (e.g., wherein the moisture pad comprises one or more ingredients selected from: witch hazel water, bisabolol lactic acid, mandelic acid, pyruvic acid, derivatives of lactic, mandelic or pyruvic acid, and combinations thereof).

1.53. The personal care composition of any of 1.34-1.52, wherein the microneedle patch can be used on a subject's: skin, lip, cheek, sublingual, tongue and combinations thereof.

1.54. The personal care composition of any of 1.34-1.53, wherein the holes or pores resulting from the use of the microneedle patch are temporary or transient.

1.55. The personal care composition of any of the preceding compositions, wherein the composition inhibits or reduces melanin synthesis without causing irritation (e.g., relative to a control or representative standard composition).

The composition of the present invention comprises hexylresorcinol in an amount of from 0.00001% to 1% by weight of the composition. In some embodiments, the hexylresorcinol is present in an amount of from 0.01% to 1%, from 0.05% to 1%, from 0.2% to 1%, from 0.4% to 1%, from 0.4% to 0.8%, from 0.4% to 0.6%, or about 0.5%, by weight of the composition.

The composition of the present invention comprises licorice extract in an amount of from 0.00001% to 0.1% by weight of the composition. In some embodiments, the licorice extract is present in an amount of from 0.001% to 0.05%, from 0.003% to 0.05%, from 0.01% to 0.05%, from 0.02% to 0.04%, about 0.03%, or 0.03125%, by weight of the composition.

In some embodiments, the weight ratio of the hexylresorcinol to the licorice extract present in the personal care composition is in the range of from 10:1 to 25:1, from 10:1 to 20:1, from 14:1 to 18:1 or about 16:1.

The skin lightening composition of the present invention may be any type of personal care composition. In certain embodiments, the composition is any composition that can be formulated into topical skin care formulations suitable for application to skin. Examples of such compositions include, but are not limited to, skin care compositions, antiperspirants, deodorants, body washes, creams, lotions, serums, liquid soaps, hand soaps, face soaps, shower gels, bar soaps, shampoos, hair conditioners, and cosmetics. The composition can comprise a single phase or can be a multi-phase system, for example a system comprising a polar phase and an oil phase, optionally in the form of a stable emulsion. The composition can be liquid, semi-solid or solid. The formulation can be provided in any suitable container and/or delivery instrument such as an aerosol can, tube or container with a porous cap, roll-on container, bottle, container with an open end, patches (e.g., microneedle patches), etc. In some embodiments, the personal care composition is a leave-on composition. For example, the leave-on composition is a cream, lotion, or serum. In other embodiments, the composition is a rinse-off composition. For example, the rinse-off composition is a liquid soap, hand soap, face soap, shower gel, body wash, shampoo, or hair conditioner.

The appropriate amounts of hexylresorcinol and licorice extract may depend on the type of the personal care composition. Leave-on composition stays on the surface of skin longer, potentially increasing the penetration and thus leading to improved efficacy. In contrast, rinse-off composition contains surfactants, which may cause skin irritation, if it is not removed. Therefore, rinse-off composition has less time of contact with the skin. To compensate for less time of contact with skin when using rinse-off compositions, rinse-off compositions may contain higher amounts of hexylresorcinol and licorice extract than leave-on compositions.

In some embodiments, the personal care composition is a leave-on composition, e.g., cream, lotion, or serum, and the hexylresorcinol is present in an amount of from 0.4% to from 1%, and the licorice extract is present in an amount of from 0.01% to 0.05%, by weight of the composition. For example, in the leave-on composition, the hexylresorcinol may be present in an amount of from 0.4% to from 0.6%, and the licorice extract may be present in an amount of from 0.02% to 0.04%, by weight of the composition. In certain embodiments, in the leave-on composition, the hexylresorcinol may be present in an amount of about 0.5% and the licorice extract may be present in an amount of about 0.3% or 0.3125%, by weight of the composition.

In some embodiments, the personal care composition is a rinse-off composition, e.g., a liquid soap, hand soap, face soap, shower gel, body wash, shampoo, or hair conditioner, and the hexylresorcinol is present in an amount of from 0.05% to from 1%, and the licorice extract is present in an amount of from 0.003% to 0.05%, by weight of the composition. For example, in the rinse-off composition, the hexylresorcinol may be present in an amount of from 0.4% to from 0.6%, and the licorice extract may be present in an amount of from 0.02% to 0.04%, by weight of the composition. In certain embodiments, in the rinse-off composition, the hexylresorcinol may be present in an amount of about 0.5% and the licorice extract may be present in an amount of about 0.3% or 0.3125%, by weight of the composition.

In some embodiments, the personal care composition may comprise additional skin lightening agents other than the hexylresorcinol and the licorice extract. For example, the addition skin lightening agents may be selected from 4-butyl resorcinol, niacinamide, tranexamic acid and bisabolol, and combinations thereof. In certain embodiments, the personal care composition, e.g., any of Composition 1.0 et seq., comprises 4-butyl resorcinol, niacinamide, tranexamic acid and bisabolol. In certain embodiments, the personal care composition, e.g., any of Composition 1.0 et seq., comprises 0.4-0.6% hexylresorcinol, 0.02-0.04% licorice extract, 0.04-0.2% 4-butyl resorcinol, 3-6% niacinamide, 1-5% tranexamic acid and 0.4-0.6% bisabolol.

However, several common skin lightening ingredients in the cosmetic market are reported to be unsafe, cytotoxic, unstable, or ineffective at low concentrations. Common lightening ingredients used today are kojic acid and hydroquinone. However, kojic acid and hydroquinone are known for their toxic action on skin cells and therefore their cosmetic use has been restricted or banned in many countries. In some embodiments, the personal care composition is free of kojic acid and hydroquinone.

Some skin lightening agents, e.g., 4-ethoxybenzaldehyde, are anti-inflammatory and suppress prostaglandin F2. In some embodiments, the personal care composition does not suppress prostaglandin F2. In some embodiments, the personal care composition is free of substituted benzaldehydes. The substituted benzaldehydes include, for example, 2-ethoxybenzaldehyde, 4-ethoxybenzaldehyde, 4-allyloxybenzaldehyde, or 4-propoxybenzaldehyde. In some embodiments, the personal are composition is free of 2-ethoxybenzaldehyde, 4-ethoxybenzaldehyde, 4-allyloxybenzaldehyde, and 4-propoxybenzaldehyde.

In some embodiments, the personal care composition is free of kojic acid, hydroquinone, and substituted benzaldehydes.

Optional ingredients that may be included in the personal care composition of the present invention include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments.

In some embodiments, the composition may comprise penetration agents selected from denatured alcohol (also referred to as anhydrous ethyl alcohol), witch hazel, urea, fatty acids, glycols, hyaluronic acid and combinations thereof. In some embodiments, the composition comprises with hazel and ethanol. In some embodiments, witch hazel is present in an amount of 5-15% and ethanol is present 10-20%, by weight of the composition. In some embodiments, witch hazel is present in an amount of 8-12%, e.g., about 10% and ethanol is present 13-17%, about 15%, by weight of the composition.

The composition may optionally contain emollients in any desired amount to achieve a desired emollient effect. Emollients are known in the art and are used to impart a soothing effect on the skin. Non-volatile emollients are preferable. Classes of non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material is phenyl trimethicone. Examples include, but are not limited to, PPG-14 butyl ether, PPG-3 myristyl ether, secondary alcohol ethoxylates, stearyl alcohol, stearic acid and salts thereof, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl) adipate), Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, sunflower seed oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide. In some embodiments, the composition comprises an oil selected from sunflower seed oil, olive oil, shear butter, jojoba oil, almond oil, grape seed oil, rose hip seed oil, mink oil, castor oil, soybean oil, mineral oil, and a combination thereof. In certain embodiment, the composition comprises sunflower seed oil.

The composition may include one or more humectants. Humectants can reduce evaporation and also contribute towards preservation by lowering water activity and can also impart desirable sweetness or flavor to compositions. Illustrative humectants may be or include, but are not limited to, glycerin, propylene glycol, polyethylene glycol, sorbitol, xylitol, or the like, or any mixture or combination thereof. In some embodiments, the compositions comprise humectants selected from polyhydric alcohols such as glycerin, 1,3-butylene glycol, 1,3-propanediol, sorbitol, xylitol or low molecular weight polyethylene glycols (PEGs), polyoxyethylenes, pentylene glycol, polyglutamic acid, hyaluronic acid and combinations thereof. In some embodiments, the composition comprises 1,3-butylene glycol, also known as 1,3-butanediol. 1,3-butylene glycol helps to solubilize hexylresorcinol, 4-butyl resorcinol and bisabolol. In certain embodiments, 1,3-butylene glycol in present in an amount of 4-6%, e.g., about 5%, by weight of the composition. In some embodiments, hyaluronic acid, e.g., in an amount of 0.1-0.3%, e.g., about 0.2%, by weight of the composition. In some embodiments, the composition comprises hyaluronic acid and 1,3-butylene glycol.

The composition may include thickeners. Illustrative thickeners may be or include, but are not limited to, sodium polyacryloyldimethyl taurate, colloidal silica, fumed silica, a cross-linked polyvinylpyrrolidone (PVP) polymer, cross-linked polyvinylpyrrolidone (PVP), or the like, or mixtures or combinations thereof. In some embodiments, the thickening system includes a cross-linked polyvinylpyrrolidone (PVP) polymer. Illustrative thickeners may also be or include, but are not limited to, carbomers (e.g., carboxyvinyl polymers), carrageenans (e.g., Irish moss, carrageenan, iota-carrageenan, etc.), high molecular weight polyethylene glycols, cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, or the like, or mixtures or combinations thereof. In some embodiments, the thickener comprises or is a gum, optionally selected from xanthan gum, carrageenan, and a combination thereof. In some embodiments, the composition comprises sodium polyacryloyldimethyl taurate. Sodium polyacryloyldimethyl taurate is sold under the name of Aristoflex® Silk polymer. Sodium polyacryloyldimethyl taurate help to improve the thickening property of the composition. Sodium polyacryloyldimethyl taurate also stabilizes multiple actives and improves the sensory and application experience. In some embodiments, sodium polyacryloyldimethyl taurate. Sodium polyacryloyldimethyl taurate is present in an amount of 1-3%, e.g., about 2%, by weight of the composition.

Gelling agents may be included in the personal care composition. Examples of gelling agents include, but are not limited to, waxes, esters of fatty acid and fatty alcohol, triglycerides, partially or fully hydrogenated soybean oil, partially or fully hydrogenated castor oil, other partial or fully hydrogenated plant oils, stearyl alcohol, or other cosmetically acceptable materials, which are solid or semi-solid at room temperature and provide a consistency suitable for application to the skin.

The composition may include polyhydroxy acids. In some embodiment, the composition comprises polyhydroxy acids selected from gluconolactone, gluconic acid, galactose, lactobionic acid, and combinations thereof. In certain embodiments, the composition comprises gluconolactone, e.g., in an amount of 1-3%, e.g., about 2%, by weight of the composition. Glucanolactone is also referred to as glucono-1,5-lactone, glucanodeltalactone or GDL.

The composition may include alpha hydroxy acids, e.g., selected from mandelic acid, glycolic acid, citric acid, lactic acid, malic acid, tartaric acid, phytic acid, hydroxycaprylic acid, hydroxycapric acid, and a combination thereof. In certain embodiments, the composition comprises lactic acid, e.g., in an amount of 4-5%, e.g., about 4%, by weight of the composition.

Antioxidants may be added to the composition, preferably to act as ingredient protectants and for maintenance of long-term stability of the composition. Examples of antioxidants include, but are not limited to citric acid, butylated hydroxytoluene, pentaerythrityl tetra-di-t-butyl hydroxyhydrocinnamate and propyl gallate. In some embodiments, the composition comprises propyl gallate.

In one embodiment, the composition may comprise a combination of pentane-1,2-diol, *Rosa Damascena* Flower extract and rose oils. The combination of Pentane-1,2-diol, *Rosa Damascena* Flower extract, and Rose Oils is sold under the trademark of Rosality™. Rosality™ has anti-pollution and anti-stress properties.

The composition may also contain polymeric materials for thickening, such as polyamides, cellulose derivatives (e.g., hydroxypropylcellulose, hydroxypropyl methyl cellulose, etc.) and natural or synthetic gums, such as polyglycerides including agar, agarose, pectin, or guars or mixtures or combinations thereof. One class of materials worthy of attention for thickening a water-immiscible phase comprises derivatives of hydrolysed starch or other polysaccharides, including in particular esterified dextrins, such as dextrin palmitate. A further class of polymers that is particularly directed to structuring an oil phase containing a silicone oil comprises polysiloxane elastomers. Suspending agents such as silicas or clays such as bentonite, montmorillonite or hectorite, including those available under the trademark Bentone can also be employed to thicken liquid compositions according to the invention. The composition can be thickened with non-polymeric organic gellants, including selected dibenzylidene alditols (e.g., dibenzylidene sorbitol).

Fragrance may be included in the personal care composition of the present invention. Any fragrance suitable for personal care use may be incorporated into the personal care composition of the invention. Fragrances tend to be relatively volatile aroma compounds which are capable of entering the gas phase at skin surface temperature.

Water may be present in the personal care composition of the present invention. Water employed in the preparation of commercial personal care compositions should be deionized and free of organic impurities. Water commonly makes up the balance of the compositions and includes about 10% to about 90%, or about 10% to about 80%, by weight of the personal care compositions. This amount of water includes the free water which is added plus that amount which is introduced with other materials such as glycerin, sorbitol or any components of the invention.

The personal care compositions of the present invention may be manufactured using methods known in the art. Typically, the ingredients are combined and optionally heated where components need to be melted. The components are mixed. Desirably, volatile materials such as fragrant materials are incorporated in the composition in the latter stages of a mixing cycle in order to avoid volatilization thereof. After mixing, the composition may be poured directly into the dispensers and the container capped to preserve the product until use. In some aspects, the personal care compositions of the disclosure (e.g., any of Composition 1.0 et seq.) are formulated for use within a patch (e.g., a microneedle patch) (e.g., a dissolvable microneedle patch).

In another aspect, the invention provides a method of suppressing melanin synthesis in melanocytes in the skin, comprising applying an effective amount of any of personal care compositions as disclosed herein, e.g., any of Compositions 1.0 et seq., to the skin.

In another aspect, the invention provides a method of treating or prophylaxis of post-inflammatory hyperpigmentation in the skin, comprising applying an effective amount of any of personal care compositions as disclosed herein, e.g., any of Compositions 1.0 et seq., to the skin.

In another aspect, the invention provides a method of treating or prophylaxis of facial dyspigmentation (e.g., melasma, UV-induced solar lentigenes, and post-inflammatory hyperpigmentation) in the skin, comprising applying an effective amount of any of personal care compositions as disclosed herein, e.g., any of Compositions 1.0 et seq., to the skin.

In another aspect, the invention provides a method of treating or prophylaxis of facial dyspigmentation in the skin, wherein the dyspigmentation is selected from the group consisting of: melasma, UV-induced solar lentigines, and post-inflammatory hyperpigmentation, comprising applying an effective amount of any of personal care compositions as disclosed herein, e.g., any of Compositions 1.0 et seq., to the skin.

In one aspect, the invention provides a method of treating and/or healing wounds on the skin surface, comprising applying an effective amount of any of personal care compositions as disclosed herein, e.g., any of Compositions 1.0 et seq., to the skin. In one aspect, the method comprises any of Compositions 1.0 et seq, wherein the composition is applied via a microneedle patch and wherein the either the personal care composition and/or the microneedle comprise hyaluronic acid (HA) (e.g., HA in the range of 5 KDa-50 KDa) (e.g., 20-30 KDa HA). In one aspect the HA is low molecular weight (e.g., 20-30 KDa) and is acetylated.

In another aspect, the invention provides the use of hexylresorcinol and the licorice extract in a personal care composition, e.g., any of personal care compositions as disclosed herein, e.g., any of Compositions 1.0 et seq., for suppressing melanin synthesis in melanocytes in the skin, wherein hexylresorcinol is present in an amount of from 0.00001% to 1% by weight of the composition and licorice extract is present in an amount of from 0.00001% to 0.09% by weight of the composition.

EXAMPLES

Example 1

In order to evaluate the melanin synthesis inhibition activity of hexylresorcinol, licorice extract and the combination thereof at certain concentrations, In vitro studies are conducted on darkly pigmented human epidermal melanocyte cell model. Darkly pigmented melanocytes cells are placed on 24-well plates. As a positive control, 0.00025% hydroquinone is used. Hexylresorcinol, licorice extract, and hydroquinone solutions are prepared as follows.

Stock Solutions:
  1% Hydroquinone is prepared by dissolving hydroquinone in deionized water at 10 mg/mL, followed by filter sterilization.
  10% Hexylresorcinol is prepared by dissolving hexylresorcinol in 100% DMSO at 100 mg/mL
  2% Licorice Extract is prepared by dissolving *Glycyrrhiza Glabra* (Licorice) Root Extract in 100% DMSO at 20 mg/mL
  2× solutions are made by mixing stock solutions with media. Right before the treatment, stock solutions are mixed with media to make the final concentrations as shown in Table 1. For combination treatment, 2× solutions of hexylresorcinol and licorice extract are mixed. For single treatment, 2× solutions are mixed with the equal volume of media. Test samples are listed in Table 1.

TABLE 1

| Test sample | Description |
| --- | --- |
| Untreated | media |
| Control | 0.00025% hydroquinone in untreated media |
| HR1 | 0.00025% hexylresorcinol in untreated media |
| HR2 | 0.0001% hexylresorcinol in untreated media |
| Lic1 | 0.00005% licorice extract in untreated media |
| Lic2 | 0.000025% licorice extract in untreated media |
| Comb1 | 0.0001% hexylresorcinol, 0.00005% licorice extract in untreated media |
| Comb2 | 0.0001% hexylresorcinol, 0.000025% licorice extract in untreated media |
| Comb3 | 0.00005% hexylresorcinol, 0.00005% licorice extract in untreated media |
| Comb4 | 0.00005% hexylresorcinol, 0.000025% licorice extract in untreated media |

0.5 ml of each test sample is directly applied to the 24-well plates in triplicates. After 5 day of treatment, melanocyte viability and melanin synthesis are measured.

Melanocyte viability is quantified using Alamar Blue solution, which is a nontoxic dye commonly used to assess cell viability. The results are shown in Table 2. Melanocyte viability is reduced less than 10% in all treatments tested.

Melanin synthesis is quantified as follows. Cells are first rinsed with PBS to remove any residual solution and 200 µl NaOH is added to each cell. The plates are shaken for 4 hours to solubilize melanin produced by melanocytes. Solubilized melanin is measured by a spectrometer at 490 nm. The results are shown in Table 2.

TABLE 2

| | | Melanin Synthesis | |
| --- | --- | --- | --- |
| Test sample | Viability | Melanin Synthesis | Change from untreated |
| untreated | 100% ± 5% | 100% ± 5.1% | 0% |
| Control | 92% ± 1% | 75.7% ± 0.9% | 24.3% |
| HR1 | 95% ± 3% | 93.1% ± 0.7% | 6.9% |
| HR2 | 105% ± 8% | 97.9% ± 2.1% | 2.1% |
| Lic1 | 91% ± 1% | 85.4% ± 1.8% | 14.6% |
| Lic2 | 97% ± 7% | 89.4% ± 1.1% | 10.6% |
| Comb1 | 100% ± 6% | 76.0% ± 1.4% | 24% |
| Comb2 | 95% ± 2% | 81.9% ± 2.2% | 18.1% |

TABLE 2-continued

| | | Melanin Synthesis | |
|---|---|---|---|
| Test sample | Viability | Melanin Synthesis | Change from untreated |
| Comb3 | 92% ± 2% | 77.8% ± 0.9% | 22.2% |
| Comb4 | 101% ± 7% | 83.8% ± 0.9% | 16.2% |

As shown in Table 2, hexylresorcinol at tested concentrations (0.0001% and 0.00025%) inhibits melanin synthesis by 2.1% and 6.9%, respectively, and licorice extract at tested concentrations (0.000025% and 0.00005%) also inhibits melanin synthesis by 10.6% and 14.6%, respectively. The combination of hexylresorcinol and licorice extract shows synergistic impact on inhibiting melanin synthesis. For example, the reduction (24%) in melanin synthesis by Comp1 (0.0001% HR+0.00005% Lic) is greater than the sum (16.7%) of the reductions by HR2 (0.0001% HR) alone and Lic1 (0.00005% Lic) alone. The reduction (18.1%) in melanin synthesis by Comp2 (0.0001% HR+0.000025% Lic) is also greater than the sum (12.7%) of the reductions by HR2 (0.0001% HR) alone and Lic2 (0.000025% Lic) alone. When melanocytes are treated with a lower concentration (0.00005%) of hexylresorcinol together with 0.000025% or 0.00005% licorice extract, the reduction in melanin synthesis is greater than the sum of the reductions by a higher concentration (0.0001%) of hexylresorcinol alone (HR2) plus 0.000025% or 0.00005% licorice extract alone (Lic1 or Lic2) (Comb3 (22.2%) vs. HR2+Lic 1 (16.7%); Comb4 (16.2%) vs. HR2+Lic2 (12.7%). These results demonstrate that the combination of hexylresorcinol and licorice extract delivers synergistic benefit to inhibit melanin synthesis in human melanocytes.

In a separate assay melanin synthesis is quantified as follows. Cells are first rinsed with PBS to remove any residual solution and 200 μl NaOH is added to each cell. The plates are shaken for 4 hours to solubilize melanin produced by melanocytes. Solubilized melanin is measured by a spectrometer at 490 nm. Several combinations of hexyl resorcinol and licorice extract demonstrate unexpected benefits with respect to melanin synthesis inhibition. The results are shown in Table 2a.

TABLE 2a

| Test sample | Melanin Synthesis Inhibition (% inhibition vs. untreated) |
|---|---|
| Untreated | — |
| Control | 20.6% |
| HR 1 | 10.4% |
| HR 2 | 10.2% |
| HR 3 | 9.3% |
| HR 4 | 8.8% |
| Lic 1 | 22.5% |
| Lic 2 | 17.7% |
| Lic 3 | 13.9% |
| Lic 4 | 11.3% |
| Comb 1 | 40.2% |
| Comb 2 | 32.5% |
| Comb 3 | 28.3% |
| Comb 4 | 22.9% |
| Comb 5 | 35.1% |
| Comb 6 | 28.4% |
| Comb 7 | 23.2% |
| Comb 8 | 19.7% |
| Comb 9 | 32.0% |
| Comb 10 | 26.1% |
| Comb 11 | 21.4% |
| Comb 12 | 18.7% |

TABLE 2b

List of the compositions of the test samples provided in Table 2a

| Test sample | Description |
|---|---|
| Untreated | media |
| Control | 0.00025% hydroquinone in untreated media |
| HR1 | 0.0002% hexylresorcinol in untreated media |
| HR2 | 0.0001% hexylresorcinol in untreated media |
| HR3 | 0.00005% hexylresorcinol in untreated media |
| HR4 | 0.00025% hexylresorcinol in untreated media |
| Lic 1 | 0.0001% licorice extract in untreated media |
| Lic 2 | 0.00005% licorice extract in untreated media |
| Lic 3 | 0.000025% licorice extract in untreated media |
| Lic 4 | 0.0000125% licorice extract in untreated media |
| Comb 1 | 0.0002% hexylresorcinol, 0.0001% licorice extract in untreated media |
| Comb 2 | 0.0002% hexylresorcinol, 0.00005% licorice extract in untreated media |
| Comb 3 | 0.0002% hexylresorcinol, 0.00002% licorice extract in untreated media |
| Comb 4 | 0.0002% hexylresorcinol, 0.0000125% licorice extract in untreated media |
| Comb 5 | 0.0001% hexylresorcinol, 0.0001% licorice extract in untreated media |
| Comb 6 | 0.0001% hexylresorcinol, 0.00005% licorice extract in untreated media |
| Comb 7 | 0.0001% hexylresorcinol, 0.00002% licorice extract in untreated media |
| Comb 8 | 0.0001% hexylresorcinol, 0.0000125% licorice extract in untreated media |
| Comb 9 | 0.00005% hexylresorcinol, 0.0001% licorice extract in untreated media |
| Comb 10 | 0.00005% hexylresorcinol, 0.00005% licorice extract in untreated media |
| Comb 11 | 0.00005% hexylresorcinol, 0.00002% licorice extract in untreated media |
| Comb 12 | 0.00005% hexylresorcinol, 0.0000125% licorice extract in untreated media |

Example 2

To evaluate the melanin synthesis inhibition activity of the combination of hexylresorcinol and licorice extract in rinse-off formula, In vitro studies are conducted on Black MelanoDerm tissue model (MatTek, Ashland, MA), which is the artificial epidermis model built using both melanocytes and keratinocytes. A cleanser formulation (Composition 1) as indicated in Table 3 is prepared.

TABLE 3

| ingredient | Composition I (wt %) |
|---|---|
| Hexylresorcinol | 0.50% |
| Licorice extract | 0.03125% |
| Demineralized Water | 63.91% |
| EDTA-Tetrasodium Salt | 0.15% |
| SLES 70% | 7.94% |
| Cocoamidopropyl Betaine | 8.38% |
| 47% Potassium Hydroxide soln. | 4.33% |
| Lauryl Acid | 4.29% |
| C12-18 Fatty Acid Blend | 2.10% |
| Myristic Acid | 1.70% |
| SODIUM BICARBONATE | 0.19% |
| SODIUM CARBONATE | 0.48% |
| PEARLIZER (DM-2000) | 1.98% |
| INULIN NATURAL ORGANIC | 0.99% |
| SHINING DROPS EMOTIONS 467353 | 1.04% |
| Sodium Chloride | 1.98% |
| Colorant | 0.00148% |

Black MelanoDerm tissues are placed on 2× 12-well MatTek plates. Every other day, tissues are treated with a cleanser (Composition 1). 2% cleanser diluted with PBS is applied to the tissue surface with agitation. Tissues are incubated for one hour at 37° C., followed by rinse-off with PBS, to mimic washing. After complete removal of bubbles, tissues are placed back in the incubator with regular media.

In a separate assay, further comparisons are made to 2% kojic acid solution, which is the industry standard for in vitro tissue testing, and market-based product that is hydroquinone free ("MB HQ Free") but contains kojic acid and other skin brightening ingredients. In total, 31 prototypes are prepared, and 26 of those are assessed in MelanoDerm™ tissues, as described above.

Composition 2 (described in Table 6), comprises: Hexylresorcinol, Licorice extract, 4-butyl resorcinol, bisabolol, tranexamic acid, lactic acid and niacinamide is selected and melanin synthesis inhibition is measured relative to untreated samples and the data is demonstrated in Table 3a:

TABLE 3a

| Test sample | Melanin Synthesis Inhibition Relative to Untreated (% inhibition) |
|---|---|
| untreated | 0% |
| Kojic Acid | 73.51% |
| Market-Based HQ Free | 67.11% |
| Composition 2 | 86.95% |

The level of a skin irritation biomarker (IL-1a) is measured at day 2 to examine whether the cleanser (Composition 1) induces any irritation. The level of IL-1a is measured by ELISA (enzyme-linked immunoassay). The data is shown in Table 4. No irritation is detected in the tissues treated with Composition 1.

TABLE 4

| | untreated | Composition 1 |
|---|---|---|
| IL-1a (pg/ml) | 100.0% ± 41.0% | 75.1% ± 6.8% |

At day 15, tissues are imaged to assess visually. The microscopic image is shown in FIG. 1. The tissues treated with Composition 1 show viable melanocytes in the tissues. Composition 1 does not impact the viability of melanocytes during the treatment.

After 2 weeks of treatment, tissues are harvested and melanin production is quantified as follows. Tissues are harvested and dissolved in Solvable solution at 95° C. and centrifuged. The amount of melanin is measured by a spectrometer at 490 nm. The result is shown in Table 5. the cleanser formulation containing 0.5% hexylresorcinol and 0.3125% licorice extract (Composition 1) inhibits melanin synthesis. The result shows that the combination of hexylresorcinol and licorice extract can suppress skin darkening even in rinse-off formulas.

TABLE 5

| | untreated | Composition 1 |
|---|---|---|
| % inhibition of melanin synthesis | 0.00% ± 6.74% | 16.72% ± 13.52% |

Example 3

Two exemplary skin lightening facial creams of the invention having the formulations as indicated in Table 6 are prepared.

TABLE 6

| Ingredients | Composition 2 (% by wt.) | Composition 3 (% by wt.) |
|---|---|---|
| Hexylresorcinol | 0.5% | 0.5% |
| Licorice extract | 0.03125% | 0.03125% |
| 4-butyl resorcinol | 0.05% | 0.05% |
| Niacinamide | 4% | 4% |
| Tranexamic acid | 1% | 5% |
| Bisabolol | 0.5% | 0.5% |
| 3-butylene glycol | 5% | 5% |
| Hyaluronic acid (e.g., 50 kDa) | 0.2% | 0.2% |
| Thickener | 2% | 2% |
| Witch hazel | 10% | 10% |
| Ethanol | 15% | 15% |
| Alpha Hydroxy Acid | 4.43% | 4.43% |
| Gluconolactone | 2% | 2% |
| Sodium hydroxide 50% | 2% | 0.75% |
| Antioxidant | 0.2% | 0.2% |
| Fragrance | 0.1% | 0.1% |
| Demineralized water | balanced | balanced |

Example 4

In one aspect, the present disclosure contemplates a dissolvable microneedle patch containing a personal care formulation that comprises the following ingredients (by wt %):

| Ingredient | Composition 4 |
|---|---|
| Hexylresorcinol | 0.1%-1% (e.g., 0.5%) |
| Licorice extract | 0.01%-0.1% (e.g., 0.03125%) |
| Olive leaf extract | 3% |
| Niacinamide | 5% |
| Tranexamic acid | 3% |
| Pomegranate extract | 0.5% |
| Lycopene | 5% |
| Acetylated Hyaluronic Acid (e.g., avg MW less than or equal to 50 kDA) | 2% |
| Bioplacenta (e.g., comprising epidermal growth factor (EGF)) | 3% |
| Ascorbic acid | 12% |
| Demineralized water | balanced |

In an alternative embodiment, the present disclosure contemplates that the dissolvable microneedle patch can further comprise a moisture pad in addition to a personal care composition, for example:

a. Personal Care Formulation (Composition 5)

| Ingredient | Composition 5 (by wt. %) |
|---|---|
| Hexylresorcinol | 0.1%-1% (e.g., 0.5%) |
| Licorice extract | 0.01%-0.1% (e.g., 0.03125%) |
| Olive leaf extract | 3% |
| Tranexamic acid | 3% |
| Pomegranate extract | 0.5% |
| Lycopene | 5% |
| Acetylated Hyaluronic Acid (e.g., avg MW less than or equal to 50 kDA) | 2% |
| Bioplacenta (e.g., comprising epidermal growth factor (EGF)) | 3% |

-continued a. Personal Care Formulation (Composition 5)

| Ingredient | Composition 5 (by wt. %) |
|---|---|
| Ascorbic acid | 12% |
| Demineralized water | balanced | b. Moisture pad comprising the following ingredients:

| Ingredient | Composition 4 |
|---|---|
| Witch hazel water | 9% |
| Bisabolol | 3% |
| Lactic acid, mandelic acid and pyruvic acid | 3.5% |
| Demineralized water | balanced |

Example 5

The ability of various molecular weights of hyaluronic acid (HA) are tested to determine their respective properties relative to wound healing and repair.

In this study, human skin (leftover from abdominal plastic surgery) is used. An N=6 skin samples are used for each test condition for statistical comparison. Before treatment with test samples and positive control (Allantoin), a controlled mean wound of about 1 mm length is created on the skin by removing epidermis using a diamond spurr tip. Four microliters of test samples or Allantoin (positive control) are applied on the wound followed by incubation of the tissue for 6 days, and then harvesting of the tissues in order for hematoxylin and eosin staining for morphological analysis. The length of the wounds are measured and values are compared for statistical comparison with untreated Day 6 (self-healing of the skin in absence of any treatment). The results of the study are demonstrated in the following table:

| Sample Type | Mean Wound Width (μm) Day 0 | Mean Wound Width (μm) Day 6 | Percent (%) Reduction in Wound Width Relative to the Untreated Day 6 |
|---|---|---|---|
| Untreated (Negative Control) | 1100 (+/−52.3) | 874 (+/−117) | — |
| Allantoin (Positive Control) | 1100 (+/−52.3) | 280 (+/−142.9) | 68% |
| 30 KDa Acetylated HA | 1100 (+/−52.3) | 319 (+/−81.2) | 63.5% |
| 20 KDa HA | 1100 (+/−52.3) | 372 (+/−81.2) | 57.4% |
| 360 KDa HA | 1100 (+/−52.3) | 437 (+/−146.1) | 49.9% |
| 1170 KDa HA | 1100 (+/−52.3) | 564 (+/−109.1) | 35.5% |
| 2000-3000 KDa HA | 1100 (+/−52.3) | 681 (+/−239.1) | 22.0% |

From the above Table, Acetylated HA demonstrates the strongest wound healing activity comparable to positive control. The improvement in wound healing is not directly linear given that 30 KDa HA (acetylated) demonstrates improved wound healing properties relative to 20 KDA HA (non-acetylated). Without being by theory, acetylation of HA may prevent its recognition (and hence degradation) by endogenous hyaluronidase enzyme that is naturally and abundantly present in skin. Low molecular weight HA (i.e., 20 KDa or 30 KDa) is a relatively small molecular as compared to larger molecular weight HA (i.e., 360 KDa and above) that is typically used in the fabrication of dissolvable microneedles. Again, without being bound by theory, small molecular weight HA is expected to show stronger and more stable interactions with cell receptors, relative to larger molecular weight HA. And these interactions may be required for the proliferation and differentiation of skin cells to renew and repair the damage.

Example 6

Composition 2 (described in Table 6) is examined for its ability to induce pigment lightening.

50 female subjects 18+ years of age of all Fitzpatrick skin types and complexion types (normal, oily, dry, combination) with mild to moderate facial dyspigmentation (melasma, UV-induced solar lentigines, post-inflammatory hyperpigmentation, etc.) are enrolled. 13/50 subjects possess skin of color. Following completion of an IRB approved informed consent, subjects are provided with the study product (Composition 2, described in Table 6) for twice daily use on the entire face and a commercially available SPF50 sunscreen for use as needed during the study. Subjects are asked to continue their self-selected cleanser, moisturizer, and facial cosmetics unchanged for the 16-week duration of the study.

The investigator uses a face map to identify a pigmented target site on the face, a sun exposed area on the face, and a sun protected area beneath the chin for a dermaspectrophotometer (DSP) measurement. The dermatologist investigator completes a baseline facial efficacy and tolerability assessment. The subjects also complete a skin tolerability assessment. 15 investigator selected subjects undergo Visia-CR photography of the front, right, and left face with standard 1 lighting. Subjects then return for evaluation at week 4, week 8, week 12, and week 16.

The dermatologist investigator assesses pigment intensity of the target spot, size of target spot, pigment extent over entire face, pigment homogeneity of entire face, sallowness, lack of brightness, lack of clarity, post-inflammatory hyperpigmentation, and overall skin dyspigmentation on a 5-point ordinal scale (0=none, 1=minimal, 2=mild, 3=moderate, 4=severe) at each visit. The investigator skin tolerability is assessed in terms of erythema, edema, and irritation on the same 5-point ordinal scale. The subjects use the same scale to assess the tolerability criteria of itching, stinging/burning, redness, and swelling.

Statistical significance is defined as p less than or equal to 0.05. The ordinal nonparametric data obtained was evaluated as change from baseline using a Wilcoxon signed rank test. The numerical DSP data is analyzed with a Student t-test.

Results

13/13 skin of color subjects successfully complete the 16-week study without noting any skin tolerability issues. Similarly, the investigator notes no skin tolerability issues. There was statistically significant (p=0.004) lightening of the target spot as early as week 4 of: 6%. This improvement continues into week 16 with a statistically significant (p<0.001) target spot lightening of: 10%. The target spot is selected as the darkest, well-demarcated pigmented area on the face. There is no lightening noted below the chin where the study product was not applied as expected. By week 16, there is also statistically significant (p=0.013) lightening of the entire face. This data confirms the ability of the study product to improve overall skin pigmentation, as well as hyperpigmented spots in skin of color.

The investigator assessed parameters also demonstrate a statistically significant 25% decrease in target spot pigment intensity (p=0.008) and 35% improvement in skin brightness (p=0.003) after 4 weeks of product use. By week 12, and continuing on into week 16, all other parameters (size of target spot, pigment extent over entire face, pigment homogeneity of entire face, sallowness, lack of clarity, and overall skin dyspigmentation) demonstrate statistically significantly improvement. Only post-inflammatory hyperpigmentation is not improved. At week 16, there is a 34% decrease in pigment intensity of the target spot, a 32% decrease in the size of the target spot, a 31% decrease in pigment extent over entire face, a 32% decrease in pigment homogeneity of entire face, a 39% decrease in facial sallowness, a 45% improvement in facial brightness, a 45% improvement in facial clarity, and a 29% improvement in overall facial skin dyspigmentation. Thus, the study product (Composition 2) is found to be highly effective at improving facial pigmentation in skin of color. Indeed, the study formulation (Composition 2) is able to reach the site of melanin production without causing noxious sensory issues or visible erythema as demonstrated by concurrent noninvasive DSP pigment bio-instrument measurements and investigator visual assessments.

Formulation is one of the biggest challenges in pigment lightening product design. For example, the active agents must penetrate to the site of pigment production without causing irritation, which could cause paradoxical pigment darkening. This is critically important, as post-inflammatory hyperpigmentation is common and difficult to treat in skin of color. Here, the study formulation is able to reach the site of melanin production without causing noxious sensory issues or visible erythema as demonstrated by concurrent noninvasive DSP pigment bio-instrument measurements and investigator visual assessments.

Example 7

Type of Study: Monadic

Methods: 50 female subjects 18+ years of age of all Fitzpatrick skin types and complexion types (normal, oily, dry, combination) with mild to moderate facial dyspigmentation (melasma, UV-induced solar lentigines, post-inflammatory hyperpigmentation, etc.) are enrolled in a 16-week study using Composition 2 ((described in Table 6) twice daily to the entire face. Subject tolerability, investigator tolerability, investigator efficacy, selected photography and dermaspectrophotometer (DSP) measurements are obtained.

Results: 48/50 subjects complete the 16-week study. A face map identifies a pigmented target site on the face, a sun exposed area on the face, and a sun protected area beneath the chin for dermaspectrophotometer (DSP) measurements. There is statistically significant (p<0.001) lightening of the target pigmented spot at weeks 4, 8, 12, and 16. The maximum pigmentation decrease seen at week 16 was 7%. No skin tolerability issues are identified. The dermatologist investigator assesses statistically significant improvement in pigment intensity of the target spot, size of target spot, pigment extent over entire face, pigment homogeneity of entire face, sallowness, lack of brightness, lack of clarity, and overall skin dyspigmentation at week 16.

Conclusions: The multimodal combination of tranexamic acid, niacinamide, and licorice root extract is effective in treating facial dyspigmentation without irritation.

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

The invention claimed is:

1. A personal care composition comprising:
penetration agents comprising witch hazel and ethanol;
hexylresorcinol; and
licorice extract;
wherein hexylresorcinol is present in an amount of from 0.00001% to 1% by weight of the composition;
wherein licorice extract is present in an amount of from 0.00001% to 0.1% by weight of the composition; and
wherein the personal care composition is free of substituted benzaldehydes.

2. The composition of claim 1, wherein the hexylresorcinol is present in an amount of from 0.2% to 1% and licorice extract is present in an amount of from 0.01% to 0.05% by weight of the composition.

3. The composition of claim 1, wherein the weight ratio of the hexylresorcinol to the licorice extract present in the personal care composition is in the range of from 10:1 to 20:1.

4. The composition of claim 1, wherein the personal care composition comprises additional skin lightening agents other than the hexylresorcinol and the licorice extract.

5. The composition of claim 4, wherein the additional skin lightening agents is selected from 4-butyl resorcinol, niacinamide, tranexamic acid and bisabolol, and a combination thereof.

6. The composition of claim 1, wherein the personal care composition comprises 0.4-0.6% hexylresorcinol, 0.02-0.04% licorice extract, 0.04-0.2% 4-butyl resorcinol, 3-6% niacinamide, 1-5% tranexamic acid and 0.4-0.6% bisabolol.

7. The composition of claim 1, wherein the personal care composition is free of kojic acid and hydroquinone.

8. The composition of claim 1, wherein the personal care composition is selected from the group consisting of creams, lotions, serums, antiperspirants, deodorants, body washes, liquid soaps, liquid hand soaps, shower gels, bar soaps, shampoos, hair conditioners, and cosmetics.

9. The composition of claim 1, wherein the licorice extract is licorice root extract.

10. The composition of claim 1, wherein the composition comprises a thickener, optionally wherein the thickener comprises sodium polyacryloyldimethyl taurate.

11. The composition of claim 1, wherein the composition comprises a humectant, optionally wherein the humectant comprises 1,3-butylene glycol.

12. The composition of claim 1, wherein the composition comprises:
0.4-0.6% hexylresorcinol;
0.02-0.04% licorice extract;
0.04-0.2% 4-butyl resorcinol;
3-6% niacinamide;
1-5% tranexamic acid;
0.4-0.6% bisabolol;
4-6% 3-butylene glycol;
0.1-0.3% hyaluronic acid;
1-3% sodium polyacryloyldimethyl taurate;
8-12% witch hazel; and
13-17% ethanol, by weight of the composition.

13. The composition of claim 1, wherein personal care composition is delivered within a microneedle patch.

14. The personal care composition of claim 13, wherein the microneedle is selected from the group consisting of: a solid microneedle, a coated microneedle, a dissolvable microneedle, a hollow microneedle, a hydrogel-forming microneedle, and combinations thereof.

15. The personal care composition of claim 14, wherein the dissolvable microneedle comprises one or more biodegradable polymer(s).

16. The personal care composition of claim 15, wherein the one or more biodegradable polymer comprises a biodegradable polymer selected from the group consisting of: cross-linked or non-cross-linked bio-absorbable and bio-compatible polymer, polyvinylpyrrolidone, polyvinyl alcohol, silkworm sericin, collagen, bio-absorbable sugar, collagen, maltose, galactose, glucose, sucrose, fructose, xylose, xylitol, sorbitol and combinations thereof.

17. The personal care composition of claim 13, wherein the microneedle patch comprises hexylresorcinol and licorice extract.

18. A method of suppressing melanin synthesis in melanocytes in the skin, comprising applying an effective amount of the composition of claim 1 to the skin.

19. The personal care composition of claim 16, wherein the bio-compatible polymer comprises hyaluronic acid.

* * * * *